United States Patent [19]

Davis

[11] Patent Number: 5,656,652
[45] Date of Patent: Aug. 12, 1997

[54] COMPOSITIONS CONTAINING HISTAMINE-$H_2$-RECEPTOR ANTAGONISTS AT LOW DOSAGE

[75] Inventor: Adrian Francis Davis, Dorking, England

[73] Assignee: SmithKline Beecham plc, Brentford, England

[21] Appl. No.: 244,847

[22] PCT Filed: Dec. 17, 1992

[86] PCT No.: PCT/GB92/02347

§ 371 Date: Jun. 15, 1994

§ 102(e) Date: Jun. 15, 1994

[87] PCT Pub. No.: WO93/12779

PCT Pub. Date: Jul. 8, 1993

[30] Foreign Application Priority Data

Dec. 20, 1991 [GB] United Kingdom ............... 9127150

[51] Int. Cl.⁶ ............................................. A61K 31/415
[52] U.S. Cl. .................... 514/400; 424/605; 424/653; 424/683; 424/684; 424/686; 424/687; 424/690; 424/692; 514/370; 514/471; 514/544; 514/547; 514/549
[58] Field of Search ................... 424/605, 653, 424/683, 684, 686, 687, 690, 692; 514/370, 400, 471, 544, 547, 549

[56] References Cited

U.S. PATENT DOCUMENTS

| | | | |
|---|---|---|---|
| 4,824,664 | 4/1989 | Tarral et al. | 424/43 |
| 4,996,222 | 2/1991 | Carlin et al. | 514/400 |
| 5,057,319 | 10/1991 | Gottwald et al. | 424/441 |
| 5,169,640 | 12/1992 | France et al. | 424/470 |
| 5,188,839 | 2/1993 | Pearmain | 424/464 |
| 5,275,823 | 1/1994 | France et al. | 424/489 |
| 5,403,830 | 4/1995 | Place | 514/184 |
| 5,407,688 | 4/1995 | Place | 424/653 |

FOREIGN PATENT DOCUMENTS

| | | |
|---|---|---|
| 0 193 400 | 9/1986 | European Pat. Off. . |
| 92/00102 | 1/1992 | WIPO . |

Primary Examiner—Gary Geist
Assistant Examiner—Barbara S. Frazier
Attorney, Agent, or Firm—Nora Stein-Fernandez; William T. King; Edward T. Lentz

[57] ABSTRACT

Compositions for oral administration for the treatment of gastric disorders comprising histamine $H_2$-receptor antagonist, and antacid, optimally buffered to promote local absorption of the $H_2$-receptor antagonist, wherein the quantity of $H_2$-receptor antagonist per unit dosage form is less than 25 mg.

10 Claims, No Drawings

COMPOSITIONS CONTAINING HISTAMINE-$H_2$-RECEPTOR ANTAGONISTS AT LOW DOSAGE

This application is a 371 of PCT/GB92/02347, filed Dec. 17, 1992.

This invention relates to the treatment of gastric disorders and pharmaceutical compositions for use therein. More particularly the invention relates to the local treatment of gastric disorders, especially acute gastric disorders such as acid indigestion, heartburn and gastritis, and gastric and peptic ulcer, using orally administrable pharmaceutical compositions comprising a histamine $H_2$-receptor antagonist contained within a drug delivery system. Compositions for use in the invention are specifically adapted to provide local delivery across the stomach wall to the $H_2$-receptor on the parietal cell receptor.

Histamine $H_2$-receptor antagonists, for example cimetidine, ranitidine, nizetidine and famotidine, reduce acid secretion by acting directly on the acid-secreting parietal cell located within the gastric gland of the stomach wall.

Although histamine $H_2$-receptor antagonists are remarkably effective in the treatment of many gastric disorders, in particular peptic and gastric ulcers, there exist certain patient groups which do not respond to treatment. In addition, the time lapse between dosing and onset of action, limits the potential benefit of histamine $H_2$-receptor antagonists in the treatment of acute, self-limiting gastric disorders.

Histamine $H_2$-receptor antagonists are of potential benefit in the self-medication of acute, self-limiting gastric disorders such as hyperacidity. However, their slow onset of action is unlikely to meet the consumer requirement for rapid relief of symptoms.

Moreover, it will be appreciated that use of high dose levels in an attempt to achieve rapid relief of symptoms is not appropriate for non-prescription use. Indeed, a reduction from the standard therapeutic dose would be desirable for self-medication.

Co-administration of histamine $H_2$-receptor antagonists and other pharmaceutically active materials, including antacids, has been investigated. The rationale for co-administration with antacid is that the antacid brings about rapid relief from the symptoms of excess stomach acidity by neutralisation whereas the histamine $H_2$-receptor antagonist acts independently by inhibiting secretion of acid from the parietal cell.

However, it is well known (Bodemar G. et al., Lancet, 1, 444–445, 1979; Mihaly G. W. et al., B. M. J., 285, 998–9, 1982; Lin. J. H. et al., B. J. Clin. Pharmacol. 24, 551–3, 1987) that when histamine $H_2$-receptor antagonists are co-administered with antacids, especially antacids with high acid-neutralising capacity, a substantial reduction in the plasma bioavailability of the histamine $H_2$-receptor antagonist is frequently observed. Histamine $H_2$-receptor antagonist—antacid combinations are therefore generally contraindicated.

EP-A-0 193 400 (Reckitt and Colman) described pharmaceutical compositions comprising mixtures of a histamine $H_2$-receptor antagonist and sodium polyacrylate in the weight ratio 10:1 to 1:10. The compositions are described for use in the treatment of gastritis or gastroduodenal ulcers. The compositions may include an antacid. Use of antacid is described as resulting in a reduction in the viscosity of the liquid compositions, thereby providing some degree of viscosity control in the design of readily pourable liquid preparations.

According to EP-A-0 193 400, the synergistic effect between the histamine $H_2$-receptor antagonist and polyacrylate affords the possibility of lower doses of the histamine $H_2$-receptor antagonist being used with a resultant reduction in side-effects. EP-A-0 193 400 discloses a normal unit dosage of histamine $H_2$-receptor antagonist in the range 800 to 10 mg in the case of cimetidine and in the range 150 to 5 mg in the case of ranitidine.

Current treatments using histamine $H_2$-receptor antagonists act systemically, i.e. the histamine $H_2$-receptor antagonist is delivered to the parietal cell receptor from the blood.

International Patent Publication No. WO 92/00102 describes oral treatment of gastric disorders using a histamine $H_2$-receptor antagonist in combination with an antacid to promote local delivery of the histamine $H_2$-receptor antagonist to the receptor of the parietal cell wall. Local delivery increases the stomach wall receptor site bioavailability of the histamine $H_2$-receptor antagonist and increases the capacity of the histamine $H_2$-receptor antagonist to reduce acid secretion compared with that of histamine $H_2$-receptor antagonist alone.

The increase in acid-secretion reducing capacity is described as being advantageous in the treatment of ulcer patients, in particular hypersecreting patients, in the treatment of those patients diagnosed as non-responders, and also to reduce the onset-phase of single-dose, self-medication for acute gastric disorders, for example gastric disorders due to hyperacidity.

International Patent Publication No. WO 92/00102 discloses a dose level of the $H_2$-receptor antagonist cimetidine from about 25 to 400 mg, typically from about 50 to 200 mg of cimetidine per dosage form. Dosage levels between 25 and 50 mg of cimetidine are lower than those currently regarded as conferring therapeutic benefit. The potential for using reduced dose levels of histamine $H_2$-receptor antagonist, brought about by synergy between the histamine $H_2$-receptor antagonist and antacid, is described as an advantageous feature of local delivery.

Surprisingly, it has now been found that a combination of histamine $H_2$-receptor antagonist and antacid is effective in increasing local stomach wall receptor site bioavailability of the histamine $H_2$-receptor antagonist through local delivery to the parietal cell tissue receptor at very low dosage levels of the histamine $H_2$-receptor antagonist so as to provide therapeutic benefit without reliance on synergy between histamine $H_2$-receptor antagonist and polyacrylate.

Accordingly, the present invention provides the use of an orally administrable pharmaceutical composition comprising a histamine $H_2$-receptor antagonist and an antacid, for the manufacture of a medicament for the treatment of gastric disorders, whereby the composition is optimally buffered to confer a pH substantially equal to that of the pKa of the histamine $H_2$-receptor antagonist, characterised in that the dose of histamine $H_2$-receptor antagonist per unit dosage form is less than 25 mg.

Histamine $H_2$-receptor antagonists for use in compositions of the invention include cimetidine, ranitidine and famotidine, preferably cimetidine and ranitidine, and especially cimeditine. pKa values for known histamine $H_2$-receptor antagonists are readily available from pharmacological publications.

The dose of histamine $H_2$-receptor antagonist may be selected according to the potency of the chosen antagonist on a weight basis and according to the severity of the condition.

A suitable dose of antagonist when cimetidine is between 1 mg and 25 mg, preferably between 1 mg and 10 mg, for example 5,10,15 or 20 mg.

A suitable dose of antagonist when ranitidine is between 1 mg and 25 mg, preferably between 1 mg and 10 mg, more preferably between 1 mg and 5 mg, for example 1,2,3,4,5, 10,15 or 20 mg.

A suitable dose of antagonist when famotidine is between 1 mg and 10 mg, preferably between 1 mg and 5 mg, for example 1,2,3,4,5,6,7,8 or 9 mg.

The invention also provides a method of treatment of gastric disorders comprising administering to a sufferer an effective amount of a locally acting pharmaceutical composition comprising a histamine $H_2$-receptor antagonist and an antacid, optimally buffered to confer a pH substantially equal to that of the pKa of the histamine $H_2$-receptor antagonist, whereby the dose of histamine $H_2$-receptor antagonist per unit dosage form is less than 25 mg.

In a further aspect, the invention provides a locally acting pharmaceutical composition for use in the treatment of gastric disorders which comprises a histamine $H_2$-receptor antagonist and an antacid, optimally buffered to confer a pH substantially equal to that of the pKa of the histamine $H_2$-receptor antagonist, whereby the dose of histamine $H_2$-receptor antagonist per unit dosage form is less than 25 mg.

Compositions for use in the invention are optimally buffered by the use of a buffering component which is suitably an antacid having equilibrium pH, acid neutralising capacity and gastric residence time values which provide a pH profile with time conferring a local pH level substantially equal to that of the pKa of the histamine $H_2$-receptor antagonist.

This approach of locally delivering $H_2$-receptor antagonists via the stomach mucosa is of particular benefit in the self-medication of acute, self-limiting gastric disorders such as hyperacidity. Local delivery according to the invention which increases the concentration of drug at the $H_2$-receptor of the parietal cell and renders the histamine $H_2$-receptor antagonist effective at very low dosage levels, is regarded as of particular benefit in the treatment of these disorders.

The above-mentioned parameters for a suitable buffering component are readily available to those skilled in the art. Suitable buffering agents for use in compositions of the invention include aluminium hydroxide, magnesium hydroxide, aluminum hydroxide-magnesium carbonate co-dried gel, magnesium carbonate, magnesium oxide, magnesium aluminium silicate, magnesium trisilicate, sodium bicarbonate, calcium carbonate, bismuth carbonate, alkali metal salts of citric, tartaric, benzoic, sorbic and phosphoric acid, and combinations thereof.

Further suitable antacids may be selected by pharmacokinetic analysis of the acid-secretion reducing capacity of a selected histamine $H_2$-receptor antagonist using a pharmacokinetic model based upon a modified, standard two-compartment model. With the introduction of further compartments to separately describe the stomach and the intestine, and with transport between the tissue compartment, representing the parietal cell tissue receptor compartment, and the stomach lumen, the model may be used to describe pharmacokinetics for a selected histamine $H_2$-receptor antagonist. The model demonstrates the reduction in local bioavailability of the histamine $H_2$-receptor antagonist at the parietal cell tissue receptor compartment as a function of gastric excretion and the increase in local bioavailability in the parietal cell tissue receptor compartment as a function of local, gastric absorption, and their dependence on gastric pH. Gastric pH levels are influenced by antacid. Thus, by inserting known values for equilibrium pH, acid neutralising capacity and gastric residence time, the suitability of any given antacid may be determined.

Conventional histamine $H_2$-receptor antagonist therapies act systemically and drug is distributed to all parts of the body via the bloodstream. Hence, it will be appreciated that non-target body tissues are exposed to drug. An advantage of a locally targeted drug delivery system is that very low doses of the histamine $H_2$-receptor antagonist may be used and thus pharmacologically relevant doses are not achieved in non-target tissues.

Excretion of histamine $H_2$-receptor antagonist into the stomach lumen from the parietal cell tissue receptor causes a reduction in local bioavailability of the antagonist whilst gastric absorption of histamine $H_2$-receptor antagonist into the parietal cell tissue receptor causes an increase in local bioavailability of the antagonist. The advantageous feature of the invention of using reduced dose levels of histamine $H_2$-receptor antagonist is brought about by buffering the histamine $H_2$-receptor antagonist in the gastric environment, effectively reducing antagonist excretion into the stomach lumen, increasing absorption from the stomach lumen, and increasing the residence time of the histamine $H_2$-receptor antagonist in the gastric environment.

It will be further appreciated that treatment with the present compositions provides a more rapid onset of action which renders them particularly suitable for the treatment of acute gastritis.

A further aspect of the invention is that the amount of antacid present in any given composition is independent of the dose of histamine $H_2$-receptor antagonist.

The level of antacid or buffering component is optimally chosen to confer a pH substantially equal to that of the pica of the histamine $H_2$-receptor antagonist.

It is a feature of the buffering component that it serves a dual role. In one aspect, in the accepted mode of action of antacids, it brings about relief from the symptoms of excess stomach acidity by neutralisation. In a second aspect, and more importantly, it serves to act as an appropriate buffered vehicle to enhance the absorption of the histamine $H_2$-receptor antagonist. The dose of buffering agent may be selected to achieve both effects.

A suitable dose range for magnesium hydroxide is from about 150 mg to 3000 mg, for example from about 300 mg to 1500 mg, such as from about 300 mg to 600 mg.

A suitable dose range for aluminum hydroxide is from about 180 mg to 3600 mg, for example from about 360 mg to 1800 mg, such as from 360 to 720 mg.

A suitable dose range for sodium bicarbonate is from about 400 mg to 8,000 mg for example from about 800 mg to 4000 mg, such as from about 800 mg to 1600 mg.

Compositions for use in the present invention may also contain pharmaceutically acceptable carriers. Compositions may be formulated for oral administration in solid or liquid form, for example as effervescent or non-effervescent powders or tablets, capsules, suspensions or dispersions. Compositions may thus be formulated by admixture with pharmaceutically acceptable vehicles additionally containing, as desired, pharmaceutically acceptable adjuvants including inter alia thickeners, preservatives, and colouring and flavouring agents.

It will be appreciated that certain pharmaceutical compositions for use in the present invention comprising very low doses of histamine $H_2$-receptor antagonist are novel and as such form a further aspect of the invention.

The following Examples illustrate the invention.

EXAMPLE 1

Powder Formulations

The ingredients are dry blended under conditions of controlled temperature and humidity using conventional equipment.

EXAMPLE 2

Tablet Formulations

The active antacid ingredients are granulated or spray dried in a conventional manner. The granule and the histamine $H_2$-receptor antagonist are blended along with conventional tabletting aids, fillers and palatability aids and the blend is tabletted on a conventional machine.

POWDER FORMULATIONS
Example 1

| | \multicolumn{6}{c}{Formulation No.} |
|---|---|---|---|---|---|---|
| | 1 | 2 | 3 | 4 | 5 | 6 |
| Cimetidine | 20 | — | — | 10 | — | — |
| Ranitidine | — | 10 | — | — | 5 | — |
| Famotidine | — | — | 2 | — | — | 1 |
| Sodium Bicarbonate | 1,500 | 1,750 | 2,000 | 750 | 875 | 1,500 |
| Citric Acid | — | — | — | — | — | — |
| Tartaric Acid | — | — | — | — | — | — |
| Flavour | 1 | 1 | 1 | 1 | 1 | 1 |
| Icing Sugar | 500 | 500 | 500 | 500 | 500 | 500 |

(all amounts in mg)

TABLET FORMULATIONS
Example 2

| | \multicolumn{9}{c}{Formulation No.} |
|---|---|---|---|---|---|---|---|---|---|
| | 7 | 8 | 9 | 10 | 11 | 12 | 13 | 14 | 15 |
| Cimetidine | 20 | — | — | 10 | — | — | 20 | — | — |
| Ranitidine | — | 10 | — | — | 5 | — | — | 10 | — |
| Famotidine | — | — | 2 | — | — | 1 | — | — | 2 |
| Aluminium Hydroxide | 700 | 800 | 750 | 350 | 400 | 375 | — | — | — |
| Magnesium Hydroxide | 700 | 800 | 750 | 350 | 400 | 375 | — | — | — |
| Calcium Carbonate | — | — | — | — | — | — | 800 | 900 | 1,000 |
| Starch | 100 | 100 | 100 | 100 | 100 | 100 | 100 | 100 | 100 |
| Icing Sugar | 250 | 250 | 250 | 250 | 250 | 250 | 250 | 250 | 250 |
| Flavour | 2 | 2 | 2 | 2 | 2 | 2 | 2 | 2 | 2 |
| Povidone | 10 | 10 | 10 | 10 | 10 | 10 | 10 | 10 | 10 |
| Magnesium Stearate | 20 | 20 | 20 | 20 | 20 | 20 | 20 | 20 | 20 |

(all amounts in mg)

I claim:

1. A pharmaceutical composition for treating gastric disorders, said composition consisting essentially of a histamine $H_2$-receptor antagonist and an antacid, wherein the composition is optimally buffered to confer a pH substantially equal to that of the pKa of the histamine $H_2$-receptor antagonist and promote local absorption of the $H_2$-receptor antagonist, characterised in that the dose of histamine $H_2$-receptor antagonist per unit dosage form is less than 25 mg.

2. The composition as claimed in claim 1 characterised in that the composition is optimally buffered with a buffering component which is an antacid having equilibrium pH, acid neutralising capacity and gastric residence time values which provide a pH profile with time conferring a local pH level substantially equal to that of the pKa of the histamine $H_2$-receptor antagonist.

3. The composition as claimed in claim 1 for treating gastric disorders in ulcer patients.

4. The composition as claimed in claim 1 for the single-dose treatment of acute gastric disorders.

5. The composition as claimed in claim 1 wherein the histamine $H_2$-receptor antagonist is cimetidine, ranitidine, or famotidine.

6. The composition as claimed in claim 5 wherein the histamine $H_2$-receptor antagonist is cimetidine.

7. The composition as claimed in claim 6 wherein the dose level of cimetidine is between 1 and 25 mg per dosage form.

8. The composition as claimed in claim 7 wherein the dose level of cimetidine is between 1 and 10 mg per dosage form.

9. The composition as claimed in claim 1 wherein the composition is buffered with aluminium hydroxide, magnesium hydroxide, aluminium hydroxide-magnesium carbonate co-dried gel, magnesium carbonate, magnesium oxide, magnesium trisilicate, sodium bicarbonate, calcium carbonate, bismuth carbonate, magnesium aluminium silicate, alkali metal salts of citric, tartaric, benzoic, sorbic or phosphoric acid, or combinations thereof.

10. A method of treating gastric disorders comprising orally administering to a sufferer an effective amount of a pharmaceutical composition, said composition consisting essentially of a histamine $H_2$-receptor antagonist and an antacid, wherein the composition is optimally buffered such that the equilibrium pH, the acid neutralising capacity and the gastric residence time values confer a pH level substantially equal to that of the pKa of the histamine $H_2$-receptor antagonist, characterised in that the dose of histamine $H_2$-receptor antagonist per unit dosage form is less than 25 mg.

* * * * *